United States Patent [19]

Blass

[11] Patent Number: 5,134,062

[45] Date of Patent: Jul. 28, 1992

[54] DIAGNOSIS OF NEURONAL DISORDERS AND SCREENING POTENTIAL THERAPEUTIC AGENTS THEREFOR

[75] Inventor: John P. Blass, Bronxville, N.Y.

[73] Assignee: Cornell Research Foundation, Inc., Ithaca, N.Y.

[21] Appl. No.: 171,783

[22] Filed: Mar. 22, 1988

[51] Int. Cl.$^5$ .......................................... G01N 33/567
[52] U.S. Cl. ................................. 435/7.21; 435/240.2; 435/948; 436/548; 436/811
[58] Field of Search .................. 435/29, 1, 7, 240.1, 435/240.2, 240.3, 948, 7.21; 436/63, 547, 548, 811; 514/878, 879

[56] References Cited

U.S. PATENT DOCUMENTS 4,666,829  5/1987  Glenner et al. .......................... 435/6
4,755,380  7/1988  Grubb et al. ........................... 424/85

OTHER PUBLICATIONS

Schwartz et al., Proc. Natl. Acad. Sci. 77(2); 1154-58, 1980.
Halegoua et al., Coll 22(2): 571-581, 1980.
Yavin et al., J. Neurochemistry 46: 794-803, 1986.
Berrill et al., Development, McGraw-Hill, New York: 1976, pp. 268-269.
Hamilton and Ham, In Vitro 13(9): 537-547, 1977.
Eagle, Science 122(3168): 501-504, 1955.
Malow et al., Clinical Research 35(3): 579A (abstract), 1987.
Dennis J. Selkoe et al., 1987, Science, vol. 235, pp. 873-876, "Conservation of Brain Amyloid Proteins in Ages Mammals and Humans with Alzheimer's Disease".
Dimitry Goldgaber et al., 1987, Science, vol. 235, pp. 877-880, "Characterization and Chromosomal Localization of a cDNA Encoding Brain Amyloid of Alzheimer's Disease".
Rudolph E. Tanzi et al., 1987, Science, vol. 235, pp. 88-84, "Amyloid B Protein Gene: cDNA, mRNA Distribution, and Genetic Linkage Near the Alzheimer Locus".
Benjamin L. Wolozin et al., 1986, Science, vol. 232, pp. 648-650, "A Neuronal Antigen in the Brains of Alzheimer Patients".
G. Peterson et al., 1986, Proc. Natl. Acad. Sci. USA, vol. 83, pp. 2758-2762, "Alterations in Calcium Content and Biochemical Processes in Cultured Skin Fibroblasts from Aged and Alzheimer Donors".
B. A. Malow et al., 1987, Clin. Res., vol. 35, p. 579A, "Carnitine in Alzheimer Disease Fibroblasts and Patients".
Ephraim Yavin et al., 1986, J. Neurochem., vol. 46, pp. 794-803, "Nerve Growth Factor and Gangliosides Stimulate the Release of Glycoproteins from PC12 Pheochromocytoma Cells".
Christine Peterson et al., 1985, New England J. Med., vol. 312, pp. 1063-1065, "Altered Calcium Uptake in Cultured Skin Fibroblasts from Patients with Alzheimer's Disease".
Christine Peterson et al., 1986, Proc. Natl. Acad. Sci. USA, vol. 83, pp. 7999-8001, "Cytosolic Free Calcium and Cell Spreading Decrease in Fibroblasts from Aged and Alzheimer Donors".
G. S. Zubenko et al., 1987, Ann. Neurol., vol. 22, pp. 237-244, "Platelet Membrane Abnormality in Alzheimer's Disease".
George S. Zubenko et al., 1987, Biol. Psychiat., vol. 22, pp. 987-994, "Temperature Dependence of the Molecular Dynamics of Platelet Membranes in Alzheimer's Disease".
George S. Zubenko et al., 1987, J. Neuropathol. Exptl. Neurol., vol. 46, pp. 407-418, "Proliferation of Internal Membranes in Platelets from Patients with Alzheimer's Disease".
Steven H. Robinson et al., 1987, Ann. Neurol., vol. 21, pp. 250-258, "Alzheimer's Disease Cells Exhibit Defective Repair of Alkylating Agent-Induced DNA Damage".
John Blass et al., 1986, In: Alzheimer's and Parkinson's Disease, A. Fisher et al., eds., Plenum Press, NY, pp. 299-308, "Biological Markers for Alzheimer's Disease".
C. Ziller et al., 1983, Cell, vol. 32, pp. 627-638, "Early Segregation of a Neuronal Precursor Cell Line in the Neural Crest as Revealed by Culture in Chemically Defined Medium".
Ludwig A. Sternberger et al., Jour. Histochem. Cytochem., vol. 18, pp. 315-333, "The Unlabeled Antibody Enzyme Method of Immunohistochemistry".
Inge Grundke-Iqbal et al., 1986, Jour. of Biological Chemistry, vol. 261, pp. 6084-6089, "Microtubule-Associated Protein Tau".
Neil R. Sims et al., 1986, pp. 451-457, "Altered Metabolic Properties of Cultured Skin Fibroblasts in Alzheimer's Disease".
William G. Johnson, 1981, Neurology, vol. 31, pp. 1453-1456, "The Clinical Spectrum of Hexosaminidase Deficiency Disease".
Michael S. Brown et al., 1986, Science, vol. 232, pp. 34-47, "A Receptor-Mediated Pathway for Cholesterol Homeostasis".
J. W. Callahan et al., 1970, "$G_{M-1}$-Gangliosidosis (Type II): Studies on a Fibroblast Cell Strains", Biochem. Med., vol. 4, pp. 295-316.

Primary Examiner—Esther L. Kepplinger
Assistant Examiner—Donna C. Wortman
Attorney, Agent, or Firm—Sterne, Kessler, Goldstein & Fox

[57] ABSTRACT

A method for diagnosing a neuronal abnormality in a person includes providing living non-neural somatic cells from the person, maintaining the cells in culture under conditions in which the cells become neuronally differentiated, and detecting in the culture a metabolic indicator associated with a symptom of the neuronal abnormality. Also, a method for assaying the effectiveness of a potential therapeutic agent for treatment of a symptom of a neuronal abnormality in a patient, the symptom being associated in the neuronal abnormality with a metabolic indicator, includes treating neuronally differentiated somatic cells with the potential therapeutic agent, and detecting the metabolic indicator in the culture.

28 Claims, No Drawings

DIAGNOSIS OF NEURONAL DISORDERS AND SCREENING POTENTIAL THERAPEUTIC AGENTS THEREFOR

This invention was made in the course of work supported in part by the U.S. government, which has certain rights in the invention.

BACKGROUND OF THE INVENTION

This invention relates to diagnosis and treatment of neuronal abnormalities.

The most common cause of disabling dementia in humans is Alzheimer s disease ("AD"). Its incidence increases sharply with aqe, and it is a major public health problem in our aging population. At present the by examination of brain tissue at autopsy. Human brain manipulation, as biopsy specimens are necessarily rare of the etiology of AD and of therapeutic approaches to disease are severely hampered by the absence of a known animal model.

Persons suffering from Alzheimer s disease show a characteristic neuropathology, including senile plaques and neurofibrillary tanqles. Neurofibrillary tangles comprise paired helical filaments ("PHF"), D. L. Selkoe et al., 1987, Science, vol. 235, pp. 873-76. A senile plaque commonly comprises a mass of disorganized neurites surrounding a deposit of extracellular filaments of an amyloid polypeptide ($\beta$ amyloid protein). D. Goldgaber et al., 1987, Science, vol. 235, pp. 877-80, and R. E. Tanzi et al., 1987, Science, vol. 235, pp. 880-84, cloned complementary DNAs for $\beta$ amyloid protein, and concluded that the $\beta$ amyloid protein gene is expressed at least at the level of mRNA in a variety of human neural and non-neural tissues. B. L. Wolozin et al., 1986, Science, vol. 232, pp. 648-50, prepared a monoclonal antibody, termed Alz-50, against homogenates of brain tissue of AD patients, that recognizes an antigen that is present in much higher concentration in certain brain regions of AD patients than in normal brain. Their data suggested that the antigen was a 68K molecular weight protein ("A-68 protein"), and that it was present in neurons involved in the formation of neuritic plagues and neurofibrillary tangles, and in some morphologically normal neurons in brains of AD patients.

A variety of cellular and molecular abnormalities are also expressed in a variety of non-neural tissues from patients having Alzheimer's disease, including cells cultured from the patient's skin. For example, C. Peterson et al., 1985, New England Jour. Med., vol. 312,pp. 1063-65, described defects in calcium homeostasis in cultured skin fibroblasts from patients with Alzheimer's disease ("AD patients") in excess of those from clinically normal subjects; C. Peterson et al., 1986, Proc. Natl. Acad. Sci. USA, vol. 83, pp. 2758-62, measured lower levels of mitochondria-dependent oxidative metabolism in cultured skin fibroblasts from AD patients than from clinically normal subjects; J. A. Kessler, 1987, Ann. Neurol., vol. 21, pp. 95-98, found lower production of a chol-inergic differentiating factor by cultured AD skin fibroblasts than by cultured normal skin fibroblasts. B. A. Malow et al., 1987, Clin. Res., vol. 35, p. 579A, described a pilot therapeutic trial showing improvement in performance by AD patients of a verbal-recall task after administration of L carnitine, and described amelioration of an abnormality in cyclic AMP production by application of L-carnitine to cultured skin fibroblasts from AD patients.

E. Yavin et al., 1986, J. Neurochem., vbl. 46, pp. 794-803, described release by PC12 pheochromocytoma cells in culture of glycoproteins, some stimulated by nerve growth factor ("NGF") and others by exogenous gangliosides in the media.

SUMMARY OF THE INVENTION

In general, the invention features, in one aspect, a method for diagnosing a neural abnormality in a person, including providing living non-neural somatic cells from the person, maintaining the cells in culture under conditions in which the cells become neuronally differentiated, and detecting in the culture a metabolic indicator associated with the neural abnormality.

In preferred embodiments, maintaining the cells in culture under conditions in which the cells become neuronally differentiated includes growing the cells in a differentiating medium; the living non-neural somatic cells are living skin cells; the differentiating medium includes nerve growth factor, preferably at a concentration in the medium between about 0.01 ng/ml and 10.0 ng/ml, and more preferably at 0.1 ng/ml; the differentiating medium includes chick embryo extract, preferably at a concentration in the medium between about 0.1% and 3%, and more preferably at 1%; the differentiating medium includes a cyclic AMP, preferably dibutyryl cyclic AMP, preferably at a concentration in the medium between about 0.01 mM and 10 mM, and more preferably at 0.1 mM; the differentiating medium includes gangliosides, preferably at a concentration in the medium between about 1.0 ng/ml and 100.0 ng/ml, and more preferably at 10.0 ng/ml; the gangliosides include a mixture of total brain gangliosides, preferably derived from bovine brain, or purified ganglioside species; and the metabolic indicator is an antigen. In a method for diagnosing Alzheimer s disease, the metabolic indicator is an antigen that reacts with an antibody to paired helical filaments, or is an antigen that reacts with the Alz-50 monoclonal antibody.

We have discovered that non-neuronal somatic cells can under appropriate conditions in culture express portions of the genome associated with neurons, that is, the cells become neuronally differentiated; and that under such conditions, cells from patients having a neuronal abnormality but not from clinically normal individuals express one or more metabolic indicators associated in vivo with neurons of patients having the neuronal abnormality. The metabolic indicator can be any detectable difference in metabolism between cells from patients having the neuronal abnormality and those from normal patients. Among such metabolic indicators are differences in cell morphology, in antigenic characteristics of the cells themselves and in metabolic products of the cells, and in the quantities of particular metabolic products of the cells. In particular, we have found that cells cultured from human skin which grow with a spindle-shaped morphology in the presence of fetal bovine serum, that is, human skin "fibroblasts", can, when maintained in culture in media that promote neuronal differentiation, produce neuron-specific enolase and neurofilaments; and that such neuronally differentiated cells from the skin of Alzheimer patients but not from clinically normal individuals express metabolic indicators associated in vivo with neurons of AD patients, namely, for example, PHF and the A-68 protein. Moreover, neuronally differentiated skin cells derived from AD patients produce, as a metabolic indicator, greater quantities of tau protein than do neuronally differentiated skin cells derived from clinically normal subjects.

The diagnostic method of the invention provides a reliable test for a neuronal abnormality. Non-neuronal tissues such as skin tissues are readily available for biopsy without harm to the subject person, and are easily brought into culture.

In another aspect, the invention features a method for assaying the effectiveness of a potential therapeutic agent for treatment of a symptom of a neuronal abnormality in a patient, the symptom being associated in the neuronal abnormality with a metabolic indicator. The method includes providing living non-neural somatic cells from the person, maintaining the cells in a culture under conditions in which the cells become neuronally differentiated, treating the neuronally differentiated cells with the potential therapeutic agent, and detecting a difference in a metabolic indicator between the culture and a culture of cells from the same person maintained and treated under the same conditions but without the therapeutic agent.

The expression by neuronally differentiated somatic cells of properties usually associated only with neurons provides a convenient model for basic neurobiological studies on cellular mechanisms, particularly in neurological disorders, and in potential therapeutic agents and their effects in individual cases.

DESCRIPTION OF THE PREFERRED EMBODIMENTS

Diagnostic Test

The method of diagnosis is generally as follows. Non-neural somatic cells from the person for whom a diagnosis is sought are obtained by clinical biopsy and cultured using well-known technigues. The cells are then maintained for a time under conditions that favor differentiation of mammalian neurons in culture. Skin cells, for example, maintained under such "neuronal differentiation" conditions, whether the cells are from clinically normal subjects or from persons diagnosed as having a particular neuronal disorder such as Alzheimer's disease, can express antigens normally associated with neurons in vivo or in culture. The neuronally differentiated cells are then assayed for a metabolic product whose production by neurons is characteristic of the particular neuronal disorder. Where the indicative metabolic product is an antigen, the assay is performed by immunocytochemical staining or by a well-known quantitative immunochemical technique, such as an enzyme-linked immunoassay (ELISA) or a radioimmunoassay. Non-antigenic metabolic indicators associated with Alzheimer's disease, for example, include decreases in calcium uptake, C. Peterson et al., 1985, New England J. Med., vol. 312, pp. 1063-1065, and in cytoplasmic free calcium levels, C. Peterson et al., 986, Proc. Natl. Acad. Sci. USA, vol. 83, pp. 999-8001; alterations in membrane fluorescence, G. S. Zubenko et al., 1987, Ann. Neurol., vol. 22, pp. 37-244, G. S. Zubenko et al., 1987, Biol. Psychiat., vol. 22, pp. 987-994; proliferation of internal membranes, G. S. Zubenko et al., 1987, J. Neuropathol. Exptl. Neurol., vol. 46, pp. 407-418; defective repair of DNA, S. H. Robinson et al., 1987, Ann. Neurol., vol. 1, pp. 250 258; and decreases in the expression of specific enzyme proteins, J. Blass et al., 1986, In: Alzheimer's and Parkinson's Diseases, A. Fisher et al., eds., Plenum Press, NY, pp. 299-308. Such products can be detected by, for example, appropriate radiochemical techniques (e.g., uptake of radioactive calcium), fluorescent probes (e.q., membrane fluorescence or cytoplasmic calcium levels), measurements of enzyme activities (e.g., enzymes expressed at reduced levels), or ultrastructural techniques (e.g., replication of membranes). A positive diagnosis for Alzheimer's disease in the person from whom the cells were obtained is indicated where the assay shows that the cells produce the indicative metabolic product.

The diagnostic method of the invention is illustrated by the following examples, in which 7 established cell lines from AD patients and 9 established cell lines from clinically normal subjects were neuronally differentiated and then were assayed for selected metabolic indicators associated with AD in vivo. These examples are intended as illustrations and not as a limitation of the claims.

Cultured human skin "fibroblasts" from normal Coriell Institute for Medical Research, Camden, N.J. They were studied in passage numbers 6 through 15 (AD cell lines AG6263, AG6264, AG5809, AG4159, AG8170, AG6848, AG6844; normal cell lines AG6858, AG0967, AG3525, AG5879, AG7376, AG4148, AG8701, AG3658, AG7375). Except where indicated, tissue culture supplies were from GIBCO, Grand Island, N.Y.

Cells were seeded at a density of $10^4/cm^2$ on tissue culture chamber slides (Lab-Tek, Miles Scientific), in Dulbecco's modified "low (1 gm/l) glucose" Eagle medium ("DMEM"), supplemented with 20% heat inactivated, double-filtered fetal bovine serum.

The cells were allowed 24 hours for attachment and preliminary growth, and then were rinsed once with Puck's saline A.

The cells were then maintained for an 5 additional 10-14 days in "basal differentiation medium", made by supplementing DMEM with 5% chick embryo extract, (Chick Embryo Extract, lyophilized, Cat. No. 620-5115 AD, GIBCO, Grand Island, N.Y.) 1% penicillin-streptomycin, 1% fungizone, 10 ug/ml qangliosides (bovine brain type II, Sigma), 0.1 mM dibutyryl cyclic AMP (Sigma), and 0.1 nq/ml of nerve growth factor ("NGF"; Collaborative Research, Bedford, Mass.), and then filtering through an 0.45 $\mu$ Nalgene filter. The cells were incubated at 37° C. in a water-saturated 5% $CO_2$:95% air atmosphere. An additional 0.1 $\mu$g NGF was added every 3-4 days. The medium was replenished as needed for optimal differentiation.

The cells were examined at intervals during the period of maintenance in differentiation medium to observe changes in their morphology. After 10-14 days, when the morphology of the cells appeared to have stabilized, the cells were washed 3 times in Dulbecco's phosphate-buffered saline ("PBS"; pH 7.4) and then fixed for one hour in 4% paraformaldehyde in 0.1M phosphate buffer, pH 7.4, to preserve the cells for later examination of morphology and for phase contrast photomicrography, and for immunocytochemical staining.

Some cells were grown and fixed as described above, except that they were maintained in an "enriched differentiation medium", prepared by supplementing the differentiating medium described above with selected components of the Brazeau medium, described in C. Ziller, 1983, Cell, vol. 32, pp. 627-38: 10 $\mu$g/ml insulin, 10 ng/ml hydrocortisone, 10 ng/ml somatostatin, 10 $\mu$g/ml transferrin, 10 $\mu$g/ml glycyl-L-histidyl-L-lysine, and 0.1 ng/ml epidermal qrowth factor ("EGF"). Cells maintained in this enriched differentiation medium were characterized by more growth in size and less marked morpholoqical changes than cells maintained in basal differentiation medium. The enriched differentiation medium and the basal differentiation medium are examples of differentiation media, as that term is used herein.

Cells obtained from normal patients and from AD patients and qrown under differentiation conditions became neuronally differentiated; that is, they expressed portions of the genome associated with neurons. For example, as described below, their morphology changed toward a morpholoqy typical of neurons in culture, and they produced neuron specific enolase and neurofilaments.

Cell Morphology

The morphology of cells from both AD patients and clinically normal subjects changed during maintenance in differentiation media from relatively spindle shaped to larger, rounder cells with more prominent nuclei. Cells qrown under non-differentiation conditions in media containing 20% fetal bovine serum maintained their characteristic fibroblast morphology. Over 10–14 days in basal differentiation medium, about one half of the cells from each donor developed a non-specific rounded morphology, about one quarter of the cells developed a triangular morphology, occasionally with a major process extending from a tip of the triangle, and about one quarter of the cells became round with processes on opposite sides of the cell. No cell division was observed in differentiation media in any of the cell lines.

Neuron-Specific Enoclase Production

Skin fibroblasts obtained and seeded as described above were grown in enriched differentiation medium, and neuron-specific enolase ("NSE") production by the neuronally differentiated cells was assayed by staining the cells by the Sternberger PAP-DAB procedure, generally as described in L. A. Sternberger et al., Jour. Histochem. Cytochem., vol. 18, pp. 315–33, using a commercial polyclonal antibody to neuron-specific enolase (Polysciences). Neuronally-differentiated cells from AD patients and from clinically normal subjects stained, while no stain appeared in controls lacking antibody or in controls in which the anti-NSE antibody had been adsorbed onto human brain extracts.

Neurofilament production

Skin fibroblasts obtained and seeded as described above were qrown in enriched differentiation medium, and neurofilament production by the neuronally differentiated cells was assayed by staining the cells by the Sternberger PAP-DAB procedure, using a commercial polyclonal antibody to neurofilaments (Polysciences). Neuronally-differentiated cells from AD patients and from clinically normal subjects stained, while no stain appeared in controls lacking antibody or in controls in which the anti-neurofilament antibody had been adsorbed onto extracts of human brain.

The metabolism of neuronally differentiated skin fibroblasts from AD patients differed from that of neuronally differentiated skin fibroblasts from clinically normal patients. For example, as described below, neuronally differentiated skin fibroblasts from AD patients, but not from clinically normal individuals, produced paired helical fibers and A-68 protein; and tau protein was produced in greater quantities by neuronally differentiated skin fibroblasts from AD patients than by those from clinically normal individuals.

Production of Paired Helical Fibers

Skin fibroblasts obtained and seeded as described above were grown in enriched differentiation medium, and production of paired helical fibers ("PHF") by the neuronally differentiated cells was assayed by staining the cells by the Sternberger PAP-DAB procedure, using a commercial polyclonal antibody to PHF (ICN), or using the monoclonal antibody to PHF described in I. Grundke-Iqbal et al., 1986, Jour. of Biological Chemistry, vol. 261, pp. 6084–89. Neuronally-differentiated cells from AD patients stained, while no stain appeared in cells from clinically normal subjects or after the anti-PHF antibody had been adsorbed onto extracts of brain from AD patients.

A-68 Protein Production

Skin fibroblasts harvested and seeded as described above were qrown in basal differentiation medium, and A-68 protein production was assayed by staining the cells with Alz-50 monoclonal antibody for A-68 protein, generally as described in B. L. Wolozin et al., 1986, Science, vol. 232, pp. 648–50, using a commercial streptavidin-biotin kit (Zymed). Neuronally-differentiated cells from AD patients stained, while no stain appeared in cells from clinically normal subjects or in normal mouse serum.

Tau Protein Production

Skin fibroblasts obtained and seeded as described above were grown in basal differentiation medium, and tau protein production was assayed by staining the cells with a polyclonal antibody recognizing phosphorylated and nonphosphorylated tau, obtained from Dr. I Grundke-Iqbal. Neuronally-differentiated cells from AD patients stained more heavily than cells from clinically normal subjects, as determined by visual inspection.

Screen for Therapeutic Agents

The method of screening for a potential therapeutic aqent is generally as follows. Somatic cells are obtained and brought into culture, and neuronally differentiated on basal differentiation medium or on enriched differentiation medium, generally as described above. Then the potential therapeutic agent is applied to the neuronally differentiated cells by techniques appropriate for the particular agent. The cells are then assayed to. determine the effect of the therapeutic application.

Other Embodiments

Other embodiments are within the following claims. For example, somatic cells other than skin cells can be used, such as, for example, lymphocytes or lymphoblasts. The differentiation medium can contain nerve qrowth factor, cyclic AMP, chick embryo extract, or gangliosides in various combinations. The differentiation medium can include, along with NGF, a growth factor other than NGF, such as, for example, a fibroblast growth factor or an epithelial growth factor. The gangliosides can be from a source other than bovine brain, and can be a single purified ganglioside species rather than a mixture.

The invention can be used for diagnosis of, and as a therapeutic screen for, neuronal abnormalities other than Alzheimer's disease, such as, for example, other diseases of the nervous system with an important hereditary component such as Huntington's disease, spinocerebellar degenerations including olivopontocerebellar atrophies, and inborn errors of metabolism such as the lipidoses.

I claim:

1. A method for screening Alzheimer's disease in a person, comprising:
   (a) providing a living fibroblast cell from said person;
   (b) maintaining said cell in culture medium under conditions and for a time sufficient such that said cell becomes neuronally differentiated; and
   (c) immunologically detecting a difference in the product of a metabolic indicator of Alzheimer's disease from said differentiated cell compared to a fibroblast cell from a peron free of Alzheimer's disease maintained in culture as a step (b).

2. The method of claim 1, wherein said culture medium comprises a nerve growth factor and a cyclic AMP.

3. The method of claim 2, wherein said culture medium further comprises a chick embryo extract.

4. The method of claim 3, wherien said culture medium further comprises a ganglioside.

5. The method of any one of claims 2, 3 or 4, wherein said culture medium further comprises a growth factor selected from the group consisting of a fibroblast growth factor or an epithelial growth factor.

6. The method of claim 2, wherein said cyclic AMP is dibutyryl cyclic AMP.

7. The method of claim 1, wherein said fibroblast cell is a skin cell.

8. The method of claim 1, wherein said metabolic indicator is a paired helical fiber.

9. The method of claim 1, wherein said metabolic indicator is a Tau protein.

10. The method of claim 1, wherein said metabolic indictor is an antigen against which the Alz-50 monoclonal antibody was specifically raised.

11. The method of claim 1, in which said metabolic indicator is detected by an antibody.

12. The method of claim 11, wherein said antibody is a polyclonal antibody.

13. The method of claim 11, wherein said antibody is a monoclonal antibody.

14. The method of claim 13, wherein said monoclonal antibody is Alz-50.

15. The method of claim 2, wherein the concentration in said medium of said nerve growth factor is initially from about 0.01 ng/ml to about 10.0 ng/ml.

16. The method of claim 15, wherein the concentration of said nerve growth factor is initially about 0.1 ng/ml.

17. The method of claim 3, wherein the concentration in said medium of said chick embryo extract is initially from about 0.01% to about 3%.

18. The method of claim 17, wherein the concentration of said chick embryo extract is initially about 1%.

19. The method of claim 2, wherein the concentration of said cyclic AMP in said medium is initially from about 0.01 mM to about 10.0 mM.

20. The method of claim 19, wherein the concentration of said cyclic AMP is initially about 0.1 mM.

21. The method of claim 4, wherein the concentration of said ganglioside in said medium is initially from about 1.0 ug/ml to about 100.0 ug/ml.

22. The method of claim 21, wherein the concentration of said ganglioside is initially about 10.0 ug/ml.

23. The method of claim 4, wherein said ganglioside comprise a mixture of total brain gangliosides.

24. The method of claim 23, wherein said total brain gangliosides are derived from bovine brain.

25. A method of screening a potential therapeutic agent for treating Alzheimer's disease, comprising:
   (a) providing a living fibroblast cell from a person suffering from Alzheimer's disease;
   (b) maintaining said cell in a culture medium under conditions and for a time sufficient such that said cell becomes neuronally differentiated;
   (c) treating said differentiated cell with said potential therapeutic agent; and
   (d) immunologically determining product of a metabolic indicator of Alzheimer's disease from said treated cells and the production of said metabolic indicator from a fibroblast cell from a person free of Alzheimer's disease maintained in culture as in step (b); and
   (e) comparing the results determined from said treated cells with the results determined from said cells maintained as in step (b) as an indication of the effect of said potential therapeutic agent.

26. The method of claim 25, wherein said culture medium comprise a nerve growth factor and a cyclic AMP.

27. The method of claim 26, wherein said culture medium further comprises a chick embryo extract.

28. The method of claim 27, wherein said culture medium further comprises a ganglioside.

* * * * *